US005777154A

United States Patent [19]
Chong et al.

[11] Patent Number: 5,777,154
[45] Date of Patent: Jul. 7, 1998

[54] METHOD FOR PREPARING 3-AMINO SUBSTITUTED CROTONATES

[75] Inventors: Joshua Anthony Chong, Lansdale; Fereydon Abdesken, Dresher; Peter Osei-Gyimah, Horsham, all of Pa.

[73] Assignee: Rohm and Haas Company, Philadelphia, Pa.

[21] Appl. No.: 748,750

[22] Filed: Nov. 14, 1996

[51] Int. Cl.$^6$ ............................................. C07C 229/30
[52] U.S. Cl. ............................................. 560/172
[58] Field of Search ........................ 560/38, 172

[56] References Cited

FOREIGN PATENT DOCUMENTS

| 5-5140060 | 6/1993 | Japan . |
| 6-321877 | 11/1994 | Japan . |
| 6-321877A | 11/1994 | Japan . |

*Primary Examiner*—Robert Gerstl
*Attorney, Agent, or Firm*—Clark R. Carpenter

[57] ABSTRACT

The present invention relates to methods for preparing 3-amino-4,4,4-trihalocrotonates and their derivatives from a 4,4,4-trihaloacetoacetate derivative and an amine or ammonium salt.

8 Claims, No Drawings

METHOD FOR PREPARING 3-AMINO SUBSTITUTED CROTONATES

The present invention relates to a method for preparing 3-amino-4,4,4-trihalocrotonates and their derivatives from a 4,4,4-trihaloacetoacetate or its analogs. 3-Substituted crotonates are valuable intermediates in the synthesis of agrochemicals, pharmaceuticals, and other industrial chemicals. 3-Amino substituted 4,4,4-trihalocrotonates are particularly useful, especially for preparation of trihalomethyl substituted heterocyclic compounds.

Japanese Patent Disclosure 06-321877A discloses a method for preparing 3-substituted amino-4,4,4-trifluorocrotonates in which a mixture of an alkyl 4,4,4-trifluoroacetoacetate and a primary amine is dehydrated in a solvent in the presence of a fatty acid. The method requires two steps: (1) formation of an intermediate amine salt of the trifluoroacetoacetate, and (2) dehydration of the salt. Overall yields are in the range of 60–65% using that method.

The present invention is a high yield method, which avoids the necessity of forming an intermediate amine salt of a trihaloacetoacetate, for preparing a 3-amino-4,4,4-trihalocrotonate. Specifically, this invention provides a method for the preparation of a 3-amino-4,4,4-trihalocrotonate compound of formula I

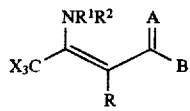

wherein

X is fluoro or chloro;

A is O, S or $NR^5$;

B is $R^6$, $OR^6$, $SR^6$ or $NR^3R^4$;

R, $R^1$, $R^2$, $R^3$, $R^4$, $R^5$ and $R^6$ are each independently H, $(C_1-C_6)$alkyl, $(C_2-C_6)$alkenyl, $(C_2-C_6)$alkynyl, phenyl or phen($C_1-C_6$)alkyl; or $(C_1-C_6)$alkyl, $(C_2-C_6)$alkenyl, $(C_2-C_6)$alkynyl, phenyl or phen($C_1-C_6$)alkyl substituted with one or more groups independently selected from halo, CN, $NO_2$, $(C_1-C_6)$alkyl, $(C_2-C_6)$alkenyl, $(C_2-C_6)$alkynyl, phenyl, phen($C_1-C_6$)alkyl, $(C_1-C_6)$alkoxy, $(C_2-C_6)$alkenyloxy, and phenoxy; or $R^1$ and $R^2$, and $R^3$ and $R^4$ may each independently be taken together with the nitrogen to which they are attached to form a five, six, or seven membered heterocyclic ring; or when A is $NR^5$ and B is $OR^6$ or $SR^6$, $R^5$ and $R^6$ may be taken together with the A=C—B group to which they are attached to form a five, six, or seven membered heterocyclic ring; or when A is $NR^5$ and B is $NR^3R^4$, $R^3$ or $R^4$ and $R^5$ may be taken together with the A=C—B group to which they are attached form a five, six, or seven membered heterocyclic ring; comprising the steps of i) forming a mixture comprising a 4,4,4-trihaloacetoacetate derivative of formula II

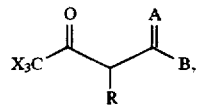

wherein

X, R, A and B are the same as defined for formula I, and an amine or ammonium salt of a weak acid of the formula

wherein $R^1$ and $R^2$ are the same as defined for formula I and $Y^-$ is the anion of a weak acid; and ii) heating the mixture.

The terms "alkyl" and "alkenyl" include straight-chain, branched-chain, and cyclic alkyl and alkenyl groups. The term "alkynyl" includes straight-chain and branched-chain alkynyl groups. The term "alkoxy" includes as the alkyl portion straight-chain, branched-chain, and cyclic alkyl groups. The term "alkenyloxy" includes as the alkenyl portion straight-chain, branched-chain, and cyclic alkenyl groups. The term "halo" means F, Cl, Br and I.

Because of their commercial utility, preferred 3-amino-4,4,4-trihalocrotonate derivatives are those wherein X is F; A is O or S; B is $OR^6$ or $SR^6$ wherein $R^6$ is $(C_1-C_6)$alkyl; $R^1$ and $R^2$ are each independently H or $(C_1-C_6)$alkyl; and R is H or $(C_1-C_6)$alkyl. Even more preferred are derivatives wherein A is O, B is $OR^6$, $R^6$ is methyl or ethyl, $R^1$ and $R^2$ are each independently H or methyl and R is H.

The preferred amine or ammonium salts are salts of organic acids such as formic, acetic, propionic, and butyric acids. Even more preferred are the amine or ammonium salts of acetic acid because of their availability.

The method is conducted with or without a solvent being present. The solvent choice is not critical if a solvent is employed. However, it should be inert to the reactants and to the reaction conditions. Preferred solvents include non-aromatic and aromatic hydrocarbons such as cyclohexane, benzene, toluene, and xylenes, ethers and polyethers such as diethyl ether and diglyme, esters such as ethyl acetate, and alcohols such as ethyl and propyl alcohol. Solvents such as alcohols, cyclohexane, and benzene are preferred because they have favorable boiling points and they are easily removed when the reaction is complete. When a hydrocarbon solvent such as cyclohexane or benzene is used, the reaction may be carried out by refluxing the reaction mixture with azeotropic removal of water, although water removal is not required. When a polar solvent such as an alcohol is used, the reaction mixture is simply refluxed over the reaction period. In either case, no acid catalyst is needed. Ethanol is a preferred solvent because it is water soluble and has a convenient boiling point.

The temperature chosen to heat the mixture depends upon the desired rate of conversion. Temperatures of from about 20° C. to about 180° C. are preferred because the reaction proceeds at a reasonable rate without unwanted side reactions. Temperatures of from 60° C. to 120° C. are more preferred because the reaction proceeds at a reasonable rate. If a solvent is used, it is convenient to chose one with a boiling point near the desired reaction temperature. In those cases the reaction can be conducted in refluxing solvent. Depending upon the solvent and amine or ammonium salt of the weak acid chosen and the reaction temperature used, the reaction is typically complete in from 1 to 24 hours.

The 3-amino-4,4,4-trihalocrotonate may be separated from the reaction mixture using common separation techniques such as distillation, solvent/solvent extraction, and solvent/water extraction. The preferred method is to separate the 3-amino-4,4,4-trihalocrotonate from the reaction mixture by a solvent/water extraction because the crotonate is typically water insoluble and the remaining unwanted reaction products and mixture components are water soluble. When the reaction is conducted using either no solvent or a water soluble solvent, it is convenient to pour the mixture directly into water when the reaction is complete and then extract the product with a water immiscible solvent.

The quantity of the amine or ammonium salt of the weak acid used is not overly critical. However, when less than one equivalent is used, based on the amount of 4,4,4-trihaloacetoacetate derivative, the reaction will not go to completion. A slight excess of the amine or ammonium salt, that is, from about 1.1 to about 4.0 equivalents, is preferred. Even more preferred is from 1.1 to 2.0 equivalents of salt.

Whether or not a solvent is employed in the process, the ammonium or amine salt of the weak acid may be formed either prior to its reaction with the 4,4,4-trihaloacetoacetate derivative using methods known to those skilled in the art or in situ from ammonia or the amine of formula $R^1R^2NH$ in the presence of the weak acid. The amount of the weak acid ranges from about 0.01 equivalent to as many equivalents as desired relative to the ammonia or amine employed in order to effect the reaction at a convenient rate.

The following examples are provided for exemplification only and are not intended to limit the scope of the invention which is defined by the claims.

EXAMPLE 1
Preparation of Ethyl 3-Amino-4,4,4-Trifluorocrotonate in Ethanol

To a stirred solution of ethyl 4,4,4-trifluoroacetoacetate (18.4 g, 0.1 mol) in ethanol (125 mL) was added ammonium acetate (30.8 g, 0.4 mol) and the mixture was refluxed for 10 hrs. After cooling to room temperature, the solution was poured into water and extracted with $CH_2Cl_2$. The organic extract was washed with aqueous $NaHCO_3$ solution, followed by water and then dried ($MgSO_4$). The solvent was removed by evaporation to give a liquid residue which was distilled to give the product as a colorless liquid; bp (atmospheric) 145°–160° C. (65°–67° C./20 torr); 16.1 g (88%); IR (neat) 3380, 3560, 1690, 1660 cm$^{-1}$. $^1$H NMR (200 MHz, $CDCl_3$) $\delta$1.3 (t, 3H); 4.18 (q, 2H); 5.15 (s, 1H); 6.2 (br s. 2H); $^{19}$F NMR (90 MHz, Acetone-d$_6$/Freon) 70.9 ppm.

EXAMPLE 2
Preparation of Ethyl 3-Amino-4,4,4-Trifluorocrotonate in Cyclohexane A mixture of ethyl 4,4,4-trifluoroacetoacetate (18.4 g, 0.1 mol), ammonium acetate (15.4 g, 0.2 mol) in dry cyclohexane (160 mL) was refluxed, with azeotropic removal of water using a Dean-Stark trap. After 6 hrs., the reaction mixture was cooled to room temperature and washed with water. The aqueous wash was extracted with methylene chloride. The methylene chloride extract was combined with the cyclohexane solution and the mixture was then dried ($MgSO_4$) and concentrated to a liquid residue using rotary evaporation. The liquid residue was distilled under reduced pressure to give the product as a colorless liquid; bp 65°–67° C./20 torr; 15.1 g (83%); IR (neat) 3380, 3560, 1690, 1660 cm$^{-1}$. $^1$H NMR (200 MHz, $CDCl_3$) $\delta$1.3 (t, 3H); 4.18 (q, 2H); 5.15 (s, 1H); 6.2 (br s. 2H); $^{19}$F NMR (90 MHz, Acetone-d$_6$/Freon) 70.9 ppm.

EXAMPLE 3
Preparation of Ethyl 3-(N-methylamino)-4,4,4-trifluorocrotonate in Ethanol To 25.6 g (0.14 mol) of ethyl 4,4,4-trifluoroacetoacetate was added 200 mL of 95% ethanol followed by 38 g (0.42 mol) of methylammonium acetate. The mixture was refluxed for 1.5 hr. Upon completion of the reaction based on gas chromatography (GC), the solvent was removed in vacuo. The residue was partitioned between 100 mL of 2% aqueous sodium hydroxide and dichloromethane (100 mL). The layers were separated and the aqueous layer was extracted once more with dichloromethane (100 mL). The dichloromethane layers were combined, dried over sodium sulfate, filtered and evaporated to dryness in vacuo to give 20 g (101 mmol, 73%) of product as a pale yellow oil. Distillation (200 mm, 100° C.) gave 17.5 g (88.8 mmol, 63%) of clear liquid. $^1$H NMR (400 MHz, $CDCl_3$) $\delta$1.2 (t, 3H), 3.0 (d, 3H), 4.1 (q, 2H), 5.1 (s, 1H), 8.2 (br. s. 1H).

EXAMPLE 4
Preparation and Isolation of Methylammonium Acetate

Methylammonium acetate was formed in either of two ways. The first involved sparging methylamine gas through a solution of 50 mL of acetic acid in 150 mL of diethyl ether at 0° C. When precipitation of the product was complete the solvent was removed in vacuo and the residue used without further purification. An alternative method used a commercial solution of 2M methylamine in tetrahydrofuran. To 50 mL (100 mmol) of this solution at 0° C. was added 6 g (100 mmol) of acetic acid. After stirring for an additional one hour the solvent was removed in vacuo and the solid methylammonium acetate was used without further purification.

EXAMPLE 5
Preparation of Ethyl 3-Amino-2-methyl-4,4,4-trifluorocrotonate in Ethanol Ethyl 2-methyl-4,4,4-trifluoroacetoacetate (10.2g, 51 mmoles), ammonium acetate (11.9, 150 mmoles), ethanol (20 g), and water (1 g) were combined in a 100 mL round-bottom flask. The mixture was heated for 6 hr. at 70° C. The mixture was then cooled to room temperature and poured into water (50 mL). The aqueous mixture was extracted with ethyl acetate (approximately 40 mL) and the layers were separated. The ethyl acetate layer was dried over anhydrous magnesium sulfate and evaporated to give an 88% yield of ethyl 3-amino-2-methyl-4,4,4-trifluorocrotonate.

EXAMPLE 6
Preparation of Ethyl 3-(N-Methylamino)-4,4,4-Trifluorocrotonate

To a stirred solution of acetic acid (57.6 g; 0.96 mol) in 250 mL of anhydrous ether, methylamine gas (31.06 g, 1.0 mol) was bubbled through, while keeping the reaction temperature at 0° C. After the amine addition, the mixture was stirred for 4 hours to complete the precipitation of the salt. The mixture was concentrated to complete dryness and then ethyl trifluoroacetoacetate (87.8 g, 0.48 mol) was mixed with the salt residue and heated with vigorous stirring at 85° C. for 5 hrs. After this period, GC analysis of the reaction mixture showed that the yield of ethyl 3-(N-methylamino)-4,4,4-trifluorocrotonate was greater than 90%.

EXAMPLE 7
Preparation of Ethyl 3-Amino-4,4,4-Trifluorocrotonate

To a stirred ethyl trifluoroacetoacetate (87.8 g, 0.48 mol) at 85° C., ammonium acetate (74 0 g, 0.96 mol) was added in portions over 1 hour such that efficient stirring of the mixture was maintained. The mixture was heated at 85° C. for an additional 4 hours. After this period, GC analysis of the reaction mixture showed that the all the ethyl trifluoroacetoacetate had been consumed and the yield of ethyl 3-amino-4,4,4-trifluorocrotonate was greater than 98%.

EXAMPLE 8
Preparation of Ethyl 3-(N-Methylamino)-4,4,4-Trifluorocrotonate

Into a stirred mixture of ethyl trifluoroacetoacetate (58.5 g; 0.318 mol) and acetic acid (19.1 g, 0.318 mol) at 85° C., methylamine gas (19.8 g, 0.636 mol) was sparged over a 1.5–2 hr period, while maintaining the reaction temperature at 85° C. The mixture was held at 85° C. for additional two hours. GC analysis of the mixture showed that all the ethyl trifluoroacetoacetate had been used up and the yield of ethyl 3-(N-methylamino)-4,4,4-trifluorocrotonate was greater than 95%.

EXAMPLE 9

Preparation of Ethyl 3-Amino-4,4,4-Trifluorocrotonate

To a stirred mixture of ethyl trifluoroacetoacetate (58.5 g; 0.318 mol) and acetic acid (19.1 g, 0.318 mol) at 85° C., ammonia gas (10.83 g, 0.636 mol) was sparged over a 1.5–2 hr period, while maintaining the reaction temperature at 85° C. The mixture was held at 85° C. for additional two hours. GC analysis of the mixture showed that all the ethyl trifluoroacetoacetate had been used up and the yield of ethyl 3-amino-4,4,4-trifluorocrotonate was greater than 98%.

It should be understood that the instant specification and examples are set forth by way of illustration and not limitation, and that various modifications and changes may be made without departing from the spirit and scope of the present invention as defined by the appended claims.

We claim:

1. A method for the preparation of a 3-amino-4,4,4-trihalocrotonate compound of formula I

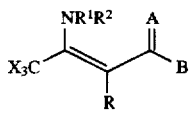

wherein

X is fluoro or chloro;

A is O, S or $NR^5$;

B is $R^6$, $OR^6$, $SR^6$ or $NR^3R^4$;

R, $R^1$, $R^2$, $R^3$, $R^4$, $R^5$ and $R^6$ are each independently H, $(C_1-C_6)$alkyl, $(C_2-C_6)$alkenyl, $(C_2-C_6)$alkynyl, phenyl or phen$(C_1-C_6)$alkyl; or $(C_1-C_6)$alkyl, $(C_2-C_6)$alkenyl, $(C_2-C_6)$alkynyl, phenyl or phen$(C_1-C_6)$alkyl substituted with one or more groups independently selected from halo, CN, $NO_2$, $(C_1-C_6)$alkyl, $(C_2-C_6)$alkenyl, $(C_2-C_6)$alkynyl, phenyl, phen$(C_1-C_6)$alkyl, $(C_1-C_6)$alkoxy, $(C_2-C_6)$alkenyloxy, and phenoxy; or $R^1$ and $R^2$, and $R^3$ and $R^4$ may each independently be taken together with the nitrogen to which they are attached to form a five, six, or seven membered heterocyclic ring; or when A is $NR^5$ and B is $OR^6$ or $SR^6$, $R^5$ and $R^6$ may be taken together with the A=C—B group to which they are attached to form a five, six, or seven membered heterocyclic ring; or when A is $NR^5$ and B is $NR^3R^4$, $R^3$ or $R^4$ and $R^5$ may be taken together with the A=C—B group to which they are attached form a five, six, or seven membered heterocyclic ring;

comprising the steps of i) forming a mixture, without a solvent being present, comprising a 4,4,4-trihaloacetoacetate derivative of formula II

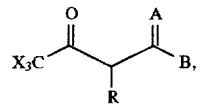

wherein

X, R, A and B are the same as defined for formula I, and an amine or ammonium salt of a weak acid of the formula $R^1R^2NH_2^+Y^-$ wherein $R^1$ and $R^2$ are the same as defined for formula I and $Y^-$ is the anion of a weak acid; and ii) heating the mixture without a solvent being present.

2. The method of claim 1 wherein X is F; A is O or S; B is $OR^6$ or $SR^6$ wherein $R^6$ is $(C_1-C_6)$alkyl; $R^1$ and $R^2$ are each independently H or $(C_1-C_6)$alkyl; and R is H or $(C_1-C_6)$alkyl.

3. The method of claim 2 wherein A is O, B is $OR^6$, $R^6$ is methyl or ethyl, $R^1$ and $R^2$ are each independently H or methyl and R is H.

4. The method of claim 1 wherein the formula $R^1R^2NH_2^+Y^-$ is an amine or ammonium salt of an organic acid.

5. The method of claim 4 wherein the organic acid is selected from formic, acetic, propionic, and butyric acid.

6. The method of claim 5 wherein the acid is acetic acid.

7. The method of claim 1 wherein the preparation is conducted at a temperature of from about 20° C. to about 180° C.

8. The method of claim 1 wherein the ammonium or amine salt of the weak acid is formed in situ from ammonia or the amine of formula $R^1R^2NH$ in the presence of the weak acid.

* * * * *